United States Patent [19]

Sander et al.

[11] Patent Number: 5,356,629

[45] Date of Patent: Oct. 18, 1994

[54] COMPOSITION FOR EFFECTING BONE REPAIR

[75] Inventors: Thomas W. Sander, Newtown; Donald S. Kaplan, Weston, both of Conn.

[73] Assignee: United States Surgical Corporation, Norwalk, Conn.

[21] Appl. No.: 728,748

[22] Filed: Jul. 12, 1991

[51] Int. Cl.$^5$ ............................ A61F 2/02; A61F 2/28
[52] U.S. Cl. ................................... 424/422; 424/423; 424/426; 523/105; 523/113; 523/115; 623/16
[58] Field of Search ....................... 523/105, 113, 115; 424/422, 423, 426; 623/16

[56] References Cited

U.S. PATENT DOCUMENTS

| | | | |
|---|---|---|---|
| 4,472,840 | 9/1984 | Jeffries | 623/16 |
| 4,485,097 | 11/1984 | Bell | 424/549 |
| 4,500,676 | 2/1985 | Balazs et al. | 424/423 X |
| 4,536,158 | 8/1985 | Bruins et al. | 523/115 X |
| 4,563,350 | 1/1986 | Nathan et al. | 424/549 |
| 4,568,536 | 2/1986 | Kronenthal et al. | 424/435 |
| 4,619,655 | 10/1986 | Hanker et al. | 623/1 |
| 4,623,553 | 11/1986 | Ries et al. | 427/2 |
| 4,642,120 | 2/1987 | Nevo et al. | 623/16 |
| 4,645,503 | 2/1987 | Lin et al. | 623/16 |
| 4,678,470 | 7/1987 | Nashef et al. | 623/16 |
| 4,705,519 | 11/1987 | Hayes et al. | 623/16 |
| 4,728,570 | 3/1988 | Ashman et al. | 428/327 |
| 4,756,907 | 7/1988 | Beck et al. | 424/433 |
| 4,774,227 | 9/1988 | Piez et al. | 514/21 |
| 4,776,890 | 10/1988 | Chu | 106/161 |
| 4,780,450 | 10/1988 | Sauk et al. | 514/2 |
| 4,846,838 | 7/1989 | Takai et al. | 623/16 |
| 4,851,521 | 7/1989 | Della Valle et al. | 424/423 X |
| 4,880,830 | 11/1989 | Rhodes | 424/470 |
| 4,888,366 | 12/1989 | Chu et al. | 523/115 |
| 4,898,734 | 2/1990 | Mathiowitz et al. | 424/426 |
| 4,912,141 | 3/1990 | Kronman | 424/423 X |
| 4,937,323 | 6/1990 | Silver et al. | 424/445 X |
| 4,962,091 | 10/1990 | Eppstein et al. | 514/2 |
| 4,969,906 | 11/1990 | Kronman | 623/16 |
| 5,001,169 | 3/1991 | Nathan et al. | 523/113 |
| 5,009,895 | 4/1991 | Lui | 424/465 |
| 5,011,692 | 4/1991 | Fujioka et al. | 424/426 |
| 5,019,398 | 5/1991 | Daste | 424/480 |
| 5,026,560 | 6/1991 | Makino et al. | 424/494 |
| 5,028,339 | 7/1991 | Clark, III | 210/688 |
| 5,037,445 | 8/1991 | Sander et al. | 623/66 |
| 5,071,436 | 12/1991 | Huc et al. | 623/16 |
| 5,108,753 | 4/1992 | Kuberasampath et al. | 424/422 |
| 5,118,528 | 6/1992 | Fessi et al. | 427/213.36 |
| 5,123,962 | 6/1992 | Komuro | 106/163.1 |
| 5,141,748 | 8/1992 | Rizzo | 424/425 |
| 5,154,927 | 10/1992 | Song et al. | 424/440 |
| 5,154,938 | 10/1992 | Broderick et al. | 426/5 |
| 5,158,934 | 10/1992 | Ammann et al. | 514/12 |
| 5,169,559 | 12/1992 | Naae et al. | 252/315.3 |
| 5,169,642 | 12/1992 | Brinker et al. | 424/488 |

FOREIGN PATENT DOCUMENTS

| | | |
|---|---|---|
| 0227627 | 7/1987 | European Pat. Off. . |
| 0233770 | 8/1987 | European Pat. Off. . |
| 309241 | 3/1989 | European Pat. Off. . |
| 329239 | 8/1989 | European Pat. Off. . |
| 2215209 | 9/1989 | United Kingdom . |

OTHER PUBLICATIONS

Annals of Plastic Surgery, vol. 21, No. 6 (Dec. 1988), pp. 576–582.
Journal of Oral Implantology, vol. 11, No. 3, (1984), pp. 371–374.
Journal of Biomedical Materials Research, vol. 23, (1989), pp. 125–133.
Journal of Oral and Maxillofacial Surgery, vol. 47, No. 1 (1989), pp. 40–45.
Science, vol. 242 (Nov. 11, 1988) pp. 885–892.
Vaandrager et al., "Craniofacial Contouring and Pectus Excavatum Correction by Porous Acrylic: Four Years of Clinical Application", pp. 656–657.
Vaandrager et al., "Porous Acrylic Cement for the Correction of Craniofacial Deformities and Repair of Defects, Animal Experimentation and Two Years of Clinical Application" (1981).
Just et al. "Cellulose Ethers", *Encyclopedia of Polymer Science and Engineering, Second Edition, vol. 3 (1985), pp. 226–269.*

Primary Examiner—Thurman K. Page
Assistant Examiner—Robert H. Harrison

[57] ABSTRACT

A composition for effecting bone repair is provided which includes biocompatible particles dispersed in a matrix.

12 Claims, No Drawings

COMPOSITION FOR EFFECTING BONE REPAIR

BACKGROUND OF THE INVENTION

The present invention is directed to a composition for effecting bone repair. More specifically, the present invention is directed to a moldable composition suitable for implantation to effect bone repair which possesses a certain degree of workability or moldability upon being wetted.

Effecting rapid, suitable repair of large bone defects caused by wounds, surgery, etc. has been a long-standing goal in the orthopedic field. One approach to effecting this repair has been implantation into bone defects of various matter which ultimately becomes an integral part of the healed bone structure, such implants being termed bone graft material. For example, U.S. Pat. No. 4,619,655 is directed to use of plaster of paris (calcium sulfate hemihydrate) as a bioresorbable scaffold for implants and bone repair, notably as scaffolding for incorporating nonresorbable particles such as hydroxyapatite into regenerated bone tissue. Collagen-based bone repair preparations including various particles such as hydroxyapatite are disclosed in U.S. Pat. Nos. 4,888,366; 4,776,890; 4,472,840; 4,563,350; 4,485,097; and 4,678,470.

The physical characteristics of such bone graft material greatly affect the handling and working thereof and also the grafting provided thereby. For example, plaster of paris will tend to lose its workability and set hard within five to ten minutes after mixing with water, making it difficult to mold over an extended period of time to properly fit within a bone defect. Additionally, plaster of paris can take over one month to be resorbed after implantation into a bone defect, which limits the rate at which bone-forming cells can take the place left by resorbed plaster of paris. Collagen tends to possess low viscosity and does not readily form a workable or moldable composition that can be appropriately shaped for implantation into bone.

Furthermore, sustained release of an active ingredient such as a medicament, therapeutic agent or drug has also been a long-pursued goal in the medical field. A sustained release composition which could be implanted within a bone defect such as a surgical or wound site and then release active ingredient over an extended period of time would be of great benefit towards effecting osteogenic healing. Precise control of resorption of a carrier in a sustained release delivery system has been difficult to attain because it has been difficult to control resorption of a matrix or carrier for the active ingredient upon implantation and after a wound or surgical opening has been closed.

SUMMARY OF THE INVENTION

It is an object of the present invention to provide for improved repair of bone and equivalent tissue upon implantation of graft material into a bone defect site.

It is also an object of the present invention to provide a composition for effecting bone repair which possesses improved moldability, workability and other handling characteristics upon being wetted with appropriate liquid medium.

It is another object of the present invention to provide for improved resorption of a composition for effecting bone repair upon implantation into the bone defect site.

These and other objects attained by the present invention are achieved by a composition suitable for effecting bone repair which comprises a plurality of biocompatible particles dispersed in a matrix selected from the group consisting of cellulose ether, collagen, hyaluronic acid, pharmaceutically acceptable salt of hyaluronic acid, derivative of hyaluronic acid and pharmaceutically acceptable salt of hyaluronic acid derivative and mixtures thereof to provide a measured stiffness of about 0.01 lb/in to about 10 lb/in when wetted with liquid medium. This wetted composition forms a moldable, semi-solid mass which can be suitably worked for implantation into bone.

The composition of the present invention, when wetted, will not set into a rock hard material like plaster of paris which, when wetted, begins to set and lose workability within five to ten minutes. Therefore, the composition of the present invention retains workability or moldability characteristics for an extended period of time after being wetted, resulting in improved overall handling characteristics and ability to be shaped upon implantation into a bone defect site. Furthermore, the matrix in the composition of the present invention can be resorbed fairly rapidly upon implantation into a bone defect site, e.g., within about ten to fourteen days after implantation, permitting faster ingrowth of osteogenic cells as bone tissue is regenerated. Moreover, this fairly rapid resorption of the matrix of the composition of the present invention can be used to deliver active ingredient dispersed or dissolved therein at a desired sustained release rate upon implantation into a bone defect site.

DESCRIPTION OF THE PREFERRED EMBODIMENTS

The matrix forming the composition of the present invention is selected from the group consisting of cellulose ether, collagen, hyaluronic acid, pharmaceutically acceptable salt of hyaluronic acid, derivative of hyaluronic acid and pharmaceutically acceptable salt of hyaluronic acid derivative and mixtures thereof. Cellulose ethers are described, e.g., in Just et al. "Cellulose Ethers": *Encyclopedia of Polymer Science and Engineering, Second Edition, Vol. 3,* (1985), pages 226-269. In particular, the cellulose ethers incorporated into the compositions of the present invention possess the ability to form moldable, semisolid compositions upon introduction of appropriate liquid medium. As used herein, the term "semi-solid" contemplates a material which, at both body temperature and at room temperature (e.g., at about 20°-40° C.), possesses the qualities of both a solid and a liquid but is more closely related to a solid, i.e., a highly viscous substance which is yet flowable to some extent such as a gel, paste, putty or clay which is capable of being molded or shaped to fit into defects of bone. Softened material is included within this definition of "semisolid".

The cellulose ethers include hydroxyalkylmethylcelluloses such as hydroxyethylmethylcellulose. Preferred cellulose ether which can be used as the matrix in the compositions of the present invention are selected from the group consisting of hydroxypropylmethylcellulose, methylcellulose and carboxymethylcellulose and mixtures thereof. Sodium carboxymethyl cellulose is the preferred form of the carboxymethylcellulose. Because of their high degree of substitution, methylcellulose ethers do not support microbial growth.

Hyaluronic acid can also be used as the matrix in the compositions of the present invention. This acid is described at Monograph No. 4634 of *The Merck Index, Ninth Edition* (1976), is solid at room temperature (about 20° C.) and forms very viscous solutions in water. Hyaluronic acid also possesses the ability to form a moldable, semisolid composition upon introduction of appropriate liquid medium. In this regard, hyaluronic acid can be used by itself as the matrix or it can be incorporated, e.g., as a thickening agent, together with cellulose ether and/or collagen as the matrix to provide the semisolid composition of desired consistency upon introduction of the appropriate liquid medium. The hyaluronic acid can be utilized in the form of a free acid or in any of its pharmaceutically acceptable salt forms, e.g., sodium hyaluronate. Additionally, certain derivatives of hyaluronic acid can be used, such as various esters and pharmaceutically acceptable salts thereof as disclosed in U.S. Pat. No. 4,851,521, e.g., methyl ester of hyaluronic acid and various pharmaceutically acceptable alkali metal and alkaline earth salts thereof. The hyaluronic acid can also be utilized in monomeric form or in polymeric form preferably having a molecular weight not greater than about one million daltons.

Collagen which can be used as the matrix in the compositions of the present invention is available in various forms. A description of collagen is found at Monograph No. 2442 of *The Merck Index, Ninth Edition* (1976) and at Piez, "Collagen": *Encyclopedia of Polymer Science and Engineering, Second Edition, Vol. 3* (1985), pages 699-727. For example, the various forms of collagen include type-I collagen which predominates in skin, tendon and bone, type-II collagen which is unique to cartilage, and type-III collagen which is found in adult skin. Preferred collagen for use as the matrix in the present invention is type-I collagen. A feature of the collagen used in the present invention herein is that it provides the semisolid composition of required stiffness value upon being wetted.

Prior to being wetted, the compositions of the present invention preferably comprise about 6 to about 36% by weight of the matrix, more preferably about 8 to about 27% by weight of the matrix, and most preferably about 10 to about 18% by weight of the matrix. After being wetted, the compositions of the present invention preferably comprise about 5% to about 20% by weight of the matrix, preferably about 6% to about 15% by weight of the matrix, and most preferably about 7% to about 10% by weight of the matrix.

The biocompatible particles which are dispersed in the matrix can be formed from either bioabsorbable or nonbioabsorbable material. Suitable bioabsorbable material which can be used to form these particles can be derived from polyglycolic acid, glycolide, lactic acid, lactide, dioxanone, e-caprolactone and trimethylene carbonate and mixtures thereof, along with various combinations of these and related monomers. Polymers of this type are known in the art, principally as materials for the fabrication of such surgical devices as sutures, wound clips, and the like, as disclosed, e.g., in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; and, 4,523,591; U.K. Patent No. 799,291; D. K. Gliding et al., "Biodegradable polymers for use in surgery—polyglycolic/poly(lactic acid) homo- and co-polymers": 1, *Polymer*, Volume 20, pages 1459-1464 (1979), and D. F. Williams (ed.), *Biocompatibility of Clinical Implant Materials*, Vol. II, ch. 9: "Biodegradable Polymers" (1981).

Copolymers of glycolide and lactide with or without additional monomers are preferred and of these glycolide-lactide copolymers are most preferred. The bioabsorbable particles can be prepared according to the procedures described in U.S. patent application Ser. No. 07/503,264 filed Apr. 2, 1990, U.S. patent application Ser. No. 07/618,652 filed Nov. 27, 1990 and U.S. patent application Ser. No. 07/654,219 filed Feb. 12, 1991.

Suitable nonbioabsorbable material which can be used to form the biocompatible particles can be derived from xenograft bone, homologous bone, autogenous bone, hydroxyapatite and polymethylmethacrylate, along with various combinations of the same. Preferred nonbioabsorbable polymer particles include particles of polymethylmethacrylate coated with polyhydroxyethylmethacrylate marketed under the trademark HTR by United States Surgical Corporation, Norwalk, Conn. The biocompatible particles of the bioabsorbable and-/or nonbioabsorbable variety are preferably incorporated into the unwetted composition in an amount of from about 94 to about 64% by weight, more preferably about 92 to about 73% by weight and most preferably about 90 to about 82% by weight. After being wetted, the composition preferably comprises from about 75% to about 35% by weight, more preferably about 70% to about 40% by weight, and most preferably about 60% to about 45% by weight of the biocompatible particles.

While biocompatible particles of any size may be utilized in the compositions of the present invention, the average size of the particles employed is preferably about 0.1 to about 3 mm, more preferably about 0.2 to about 1.5 mm, and most preferably about 0.3 to about 1.0 mm. However, particles having average sizes of about 7000 to 8000 microns, or even as small as about 100 to 700 microns, can be utilized in the compositions of the present invention.

Additionally, one or more bioactive substances can be incorporated into the compositions of the present invention, either directly into the matrix prior to or after wetting, or into the biocompatible particles, e.g., the bioabsorbable or polymethylmethacrylate particles at the time such particles are being manufactured. For example, polymethylmethacrylate particles that are coated with polyhydroxyethylmethacrylate particles can be soaked in a bath carrying a therapeutic drug or protein to incorporate this active ingredient into the coating.

Thus, it is within the scope of this invention to incorporate one or more medico-surgically useful substances into the composition, e.g., those substances which accelerate or beneficially modify the healing process when the composite is applied to a surgical repair site. So, for example, the composition of the present invention can carry a therapeutic agent which will be deposited at the repair site. The therapeutic agent can be chosen for its antimicrobial properties, capability for promoting repair or reconstruction and/or new tissue growth or for specific indications such as thrombosis. Antimicrobial agents such as broad spectrum antibiotics (gentamycin sulphate, erythromycin or derivatized glycopeptides) which are slowly released into the tissue can be applied in this manner to aid in combating clinical and sub-clinical infections in a tissue repair site.

To promote repair and/or tissue growth, one or several growth promoting factors can be introduced into the composition, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system. The bioactive substance can also be an osteogenic agent which stimulates or accelerates generation of bone upon implantation into a bone defect site. Such osteogenic agent includes osteoinductive protein, demineralized bone powder, in addition to morselized cancellous bone, aspirated bone marrow, and other autogenous bone sources.

The compositions of the present invention are specifically formulated to possess a measured stiffness, upon wetting, of about 0.01 lb/in to about 10 lb/in, more preferably about 0.05 lb/in to about 5 lb/in and most preferably about 0.1 lb/in to about 3.0 lb/in. In other words, the amounts of biocompatible particles and matrix are chosen to provide these measured stiffness values upon wetting. The stiffness value can be measured with an Instron Model 1011 available from Instron Corp., Canton, Mass., and utilizing a ten pound transducer for the measurement.

The compositions of the present invention can be prepared in any suitable fashion. For example, a dry powder-like form of the matrix material and the biocompatible particles are first mixed together to ensure uniform distribution of the biocompatible particles within the matrix. These cellulose ethers, collagen, hyaluronic acid and salts and derivatives of hyaluronic acid are all available in powder-like form. Alternatively, these matrix materials can be conveniently comminuted to the appropriate particle size of mixing. Then, the liquid medium is added to the resulting mixture to provide the moldable, semisolid composition which can then be implanted and shaped in a bone defect site.

The amount of liquid medium which can be introduced, based on the total weight of the wetted moldable composition, is preferably about 5 to about 60% by weight, more preferably about 15 to about 54% by weight and most preferably about 30 to about 48% by weight. The liquid medium introduced into the composition which interacts with the matrix to form the moldable composition can be a hydrating medium, i.e., contains water, so that compatibility of the moldable composition will be enhanced with a body into which the composition is implanted. In this regard, the liquid medium is preferably selected from water, saline solution, blood or any combination of these. Additionally, polyoxyethylene-polyoxypropylene block copolymer marketed under the name Poloxamer or Pluronic by BASF Wyandotte, Mich. can be incorporated into the matrix as the suitable liquid medium either alone or together with water, saline solution, blood, etc.

The liquid medium can be added to the composition of the present invention just before implantation into a bone defect, e.g., during surgery. For example, blood from a patient can be added into the composition during the surgical procedure with the resulting moldable, wetted composition then being introduced and shaped in a bone defect, e.g., with a surgical spatula. Once wetted, the compositions of the present invention will always remain in moldable semisolid form as long as not permitted to dry out. Thus, the fluid environment present within a living body will ensure that the moldable composition will remain in semisolid form until suitable resorption of the matrix has taken place and/or regenerated bone tissue has been formed.

The present invention will be explained in greater detail below with reference to the following examples:

EXAMPLE 1

Carboxymethylcellulose powder was mixed with particles of polymethylmethacrylate coated with polyhydroxyethylmethacrylate. Water was then added and all ingredients were thoroughly mixed to form a putty having the following composition:

| Ingredient | Amount (g) | Weight % |
| --- | --- | --- |
| polymethylmethacrylate particles coated with polyhydroxyethylmethacrylate | 3 | 55 |
| carboxymethylcellulose | 0.5 | 9 |
| water | 2 | 36 |

EXAMPLE 2

The procedure of Example 1 was repeated with methylcellulose substituted for the carboxymethylcellulose to provide a putty having the following composition:

| Ingredient | Amount (g) | Weight % |
| --- | --- | --- |
| polymethylmethacrylate particles coated with polyhydroxyethylmethacrylate | 5 | 57 |
| methylcellulose | 0.75 | 8 |
| water | 3 | 35 |

EXAMPLE 3

A putty having the following composition is prepared according to the procedure of Example 1:

| Ingredient | Amount (g) | Weight % |
| --- | --- | --- |
| particles of glycolide-lactide copolymer having 10 mole % glycolide and 90 mole % lactide | 3 | 55 |
| carboxymethylcellulose | 0.5 | 9 |
| water | 2 | 36 |

EXAMPLE 4

A putty having the following composition is prepared according to the procedure of Example 1:

| Ingredient | Amount (g) | Weight % |
| --- | --- | --- |
| particles of glycolide-lactide copolymer having 10 mole % glycolide and 90 mole % lactide | 5 | 57 |
| methylcellulose | 0.75 | 8 |
| water | 3 | 35 |

EXAMPLE 5

The following ingredients were mixed according to Example 1 to prepare a putty having the following composition:

| Ingredient | Amount (g) | Weight % |
|---|---|---|
| particles of polymethylmethacrylate coated with polyhydroxyethylmethacrylate | 2.18 | 55 |
| hydroxypropylmethylcellulose | 0.36 | 9 |
| water | 1.45 | 36 |

EXAMPLE 6

The following ingredients were mixed according to Example 1 to prepare a putty having the following composition:

| Ingredient | Amount (g) | Weight % |
|---|---|---|
| particles of polymethylmethacrylate coated with polyhydroxyethylmethacrylate | 2.18 | 55 |
| collagen having an average particle size of about 2 mm. | 0.36 | 9 |
| water | 1.45 | 36 |

EXAMPLE 7

The following ingredients were mixed according to Example 1 to prepare a putty having the following composition:

| Ingredient | Amount (g) | Weight % |
|---|---|---|
| particles of polymethylmethacrylate coated with polyhydroxyethylmethacrylate | 1.85 | 46 |
| hyaluronic acid, sodium salt of molecular weight about six hundred thousand daltons | 0.31 | 8 |
| water | 1.85 | 46 |

EXAMPLE 8

The following ingredients were mixed according to Example 1 to prepare a putty having the following composition:

| Ingredient | Amount (g) | Weight % |
|---|---|---|
| particles of polymethylmethacrylate coated with polyhydroxyethylmethacrylate | 1.85 | 52 |
| hyaluronic acid, sodium salt of molecular weight about six hundred thousand daltons | 0.31 | 9 |
| water | 1.40 | 39 |

EXAMPLE 9

The following ingredients were mixed according to Example 1 to prepare a putty having the following composition:

| Ingredient | Amount (g) | Weight % |
|---|---|---|
| particles of polymethylmethacrylate coated with polyhydroxyethylmethacrylate | 2.01 | 50 |
| hyaluronic acid, sodium salt | 0.16 | 4 |
| of molecular weight about six hundred thousand daltons | | |
| hydroxypropylmethylcellulose | 0.16 | 4 |
| water | 1.67 | 42 |

EXAMPLE 10

The following ingredients were mixed according to Example 1 to prepare a putty having the following composition:

| Ingredient | Amount (g) | Weight % |
|---|---|---|
| particles of polymethylmethacrylate coated with polyhydroxyethylmethacrylate | 2.01 | 55.4 |
| hyaluronic acid, sodium salt of molecular weight about six hundred thousand daltons | 0.16 | 4.4 |
| hydroxypropylmethylcellulose | 0.16 | 4.4 |
| water | 1.30 | 35.8 |

EXAMPLE 11

The putty-like compositions prepared in Examples 5–10 were examined for stiffness values utilizing an Instron Model 1011 with a ten pound transducer available from Instron Corp., Canton, Mass. After the water was added to each of the respective compositions of Examples 3–8, the compositions were each stirred for about 45 seconds to one minute. Then, the resulting putties were each molded into a 0.5 inch diameter × 1.0 inch long cylinder within about 1.0 to 1.5 minutes. Further measurements of the dimensions of these respective cylinders were completed within about 1.25 to 2 minutes.

These measurements were entered into the Instron computer while the crosshead of the Instron device was adjusted to be situated just above each putty of Examples 3–8 and was then moved downwardly 0.5 inches at a constant speed of 0.5 inches/minute during the evaluation (ambient temperature was about 70° F.). Six specimens of each of the compositions of Examples 5, 6, 7 and 9 were tested in this fashion, while four specimens of each of the compositions of Examples 8 and 10 were tested. The Instron device reported the stiffness values for each specimen while the computer of the Instron device calculated the average stiffness value for each group of specimens.

The stiffness values, in lb/in, for each of these specimens tested, is reported in Table I below:

TABLE I

| | Stiffness Values (lb/in) | | | | | |
|---|---|---|---|---|---|---|
| | Example No. | | | | | |
| Specimen No. | 5 | 6 | 7 | 8 | 9 | 10 |
| 1 | 2.014 | 2.630 | 0.285 | 0.733 | 0.626 | 1.229 |
| 2 | 2.489 | 2.588 | 0.136 | 0.649 | 0.222 | 1.085 |
| 3 | 1.545 | 3.339 | 0.144 | 0.408 | 0.338 | 1.154 |
| 4 | 1.179 | 2.018 | 0.144 | 0.277 | 0.230 | 0.728 |
| 5 | 2.097 | 2.914 | 0.144 | — | 0.576 | — |
| 6 | 1.538 | 2.961 | 0.081 | — | 0.250 | — |

The average stiffness values for each of the compositions of Examples 5–10 are reported in Table II below:

TABLE II

| Example No. | Average Stiffness Value (lb/in) |
|---|---|
| 5 | 1.810 |
| 6 | 2.743 |
| 7 | 0.155 |
| 8 | 0.517 |
| 9 | 0.374 |
| 10 | 1.049 |

What is claimed is:

1. A composition suitable to effect bone repair comprising from about 64 to about 94% by weight of biocompatible particles dispersed in from about 6 to about 36% by weight of a matrix selected from the group consisting of cellulose ether, collagen, hyaluronic acid, pharmaceutically acceptable salt of hyaluronic acid, ester of hyaluronic acid and pharmaceutically acceptable salt of hyaluronic acid ester and mixtures thereof to provide a measured stiffness of about 0.01 lb/in to about 10 lb/in when wetted with liquid medium,
   wherein said biocompatible particles are formed from polymethylmethacrylate coated with polyhydroxyethylmethacrylate,
   whereby said composition, when wetted, forms a moldable semi-solid mass which can be suitably worked for implantation into bone and will remain in moldable semi-solid form as long as not permitted to dry out.

2. The composition of claim 1 comprising from about 8% to about 27% by weight of said matrix and about 73% to about 92% by weight of said particles.

3. The composition of claim 2 comprising from about 10% to about 18% by weight of said matrix and about 82% to about 90% by weight of said particles.

4. The composition of claim 1 additionally comprising at least one ingredient selected from the group consisting of antimicrobial agents, growth promoting factor and osteogenic agent and mixtures thereof.

5. The composition of claim 1 having a measured stiffness of about 0.05 lb/in to about 5 lb/in when wetted.

6. The composition of claim 5 having a measured stiffness of about 0.1 lb/in to about 3.0 lb/in when wetted.

7. The composition of claim 1 being in moldable form.

8. The composition of claim 1 wherein the liquid medium contains water.

9. The composition or claim 1, additionally comprising about 5% to about 60% by weight of wetting liquid medium in the total composition.

10. A wetted composition suitable for effecting bone repair, comprising
    (i) about 5 to about 60% by weight of wetting liquid medium,
    (ii) about 75 to about 35 % by weight of biocompatible particles of polymethylmethacrylate coated with polyhydroxyethylmethacylate, and
    (iii) about 5 to about 20% by weight of a matrix selected from the group consisting of cellulose ether, collagen, hyaluronic acid, pharmaceutically acceptable salt of hyaluronic acid, ester of hyaluronic acid, pharmaceutically acceptable of hyaluronic acid ester and mixtures thereof, the biocompatible particles (ii) being dispersed in the matrix (iii),
    said composition having a measured stiffness of about 0.01 lb/in to about 10 lb/in,
    whereby said composition forms a moldable semi-solid mass which can be suitably worked for implantation into bone and will remain in semi-solid form as long as not permitted to dry out.

11. The composition of claim 10 comprising
    (i) about 15 to about 54% by weight of the wetting liquid medium,
    (ii) about 70 to about 40% by weight of the particles, and
    (iii) about 6 to about 15% by weight of the matrix.

12. The composition of claim 11 comprising
    (i) from about 30 to about 48% by weight of the wetting liquid medium,
    (ii) about 60 to about 45% by weight of the particles, and
    (iii) about 7% to about 10% by weight of the matrix.

* * * * *